US009513356B2

(12) United States Patent
Kamada et al.

(10) Patent No.: US 9,513,356 B2
(45) Date of Patent: *Dec. 6, 2016

(54) MAGNETIC RESONANCE IMAGING APPARATUS AND RECONSTRUCTED IMAGE ACQUISITION METHOD

(75) Inventors: Yasuhiro Kamada, Tokyo (JP); Masahiro Takizawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 430 days.

This patent is subject to a terminal disclaimer.

(21) Appl. No.: 14/113,259

(22) PCT Filed: May 9, 2012

(86) PCT No.: PCT/JP2012/061838
§ 371 (c)(1),
(2), (4) Date: Oct. 22, 2013

(87) PCT Pub. No.: WO2012/160971
PCT Pub. Date: Nov. 29, 2012

(65) Prior Publication Data
US 2014/0361771 A1 Dec. 11, 2014

(51) Int. Cl.
*G01V 3/00* (2006.01)
*G01R 33/56* (2006.01)
(Continued)

(52) U.S. Cl.
CPC ............... *G01R 33/56* (2013.01); *A61B 5/055* (2013.01); *G01R 33/381* (2013.01);
(Continued)

(58) Field of Classification Search
CPC ..... G01R 33/56; G01R 33/381; G01R 33/385; G01R 33/4818; G01R 33/4824; G01R 33/5617; A61B 5/055
(Continued)

(56) References Cited

U.S. PATENT DOCUMENTS 6,144,201 A * 11/2000 Miyazaki ............ G01R 33/5673
324/306
6,671,536 B2 * 12/2003 Mistretta ................ G01R 33/28
324/309
(Continued)

FOREIGN PATENT DOCUMENTS

| CN | 101232845 A | 7/2008 |
| JP | 2009-131613 | 6/2009 |
| JP | 2011-167509 | 9/2011 |

OTHER PUBLICATIONS

Feb. 10, 2015 Chinese official action in corresponding Chinese Patent Application No. 201280022055.1.
(Continued)

*Primary Examiner* — Susan Lee
(74) *Attorney, Agent, or Firm* — Cooper & Dunham LLP

(57) ABSTRACT

In order to improve contrast and image quality in non-orthogonal measurement without sacrificing speed, in imaging which combines a fast imaging sequence for acquiring a plurality of echo signals in one shot with non-orthogonal system measurement, the shape of a blade in which an echo train of each shot is arranged includes a fan-shaped region having the radius and the arc of a circle centered on the origin of the k space, and a region overlapping an adjacent blade. During measurement, control is performed such that an echo signal for desired TE of each blade is arranged in a low spatial frequency region of a k space, and during image reconstruction, body motion between the blades is corrected using data of the overlapping regions.

15 Claims, 16 Drawing Sheets

(51) Int. Cl.
- *A61B 5/055* (2006.01)
- *G01R 33/48* (2006.01)
- *G01R 33/381* (2006.01)
- *G01R 33/385* (2006.01)
- G01R 33/561 (2006.01)

(52) U.S. Cl.
CPC ....... *G01R 33/385* (2013.01); *G01R 33/4818* (2013.01); *G01R 33/4824* (2013.01); *G01R 33/5617* (2013.01)

(58) Field of Classification Search
USPC .......................................................... 324/309
See application file for complete search history.

(56) References Cited

U.S. PATENT DOCUMENTS

| | | | |
|---|---|---|---|
| 6,894,494 B2 * | 5/2005 | Stergiopoulos .... | G01R 33/5673 324/309 |
| 7,535,222 B2 * | 5/2009 | Bammer ............ | G01R 33/4824 324/307 |
| 7,622,926 B2 * | 11/2009 | Taniguchi .......... | G01R 33/4824 324/309 |
| 7,692,423 B2 * | 4/2010 | Cunningham ..... | G01R 33/5676 324/307 |
| 7,786,728 B2 | 8/2010 | Fukuta | |
| 8,344,729 B2 | 1/2013 | Takizawa et al. | |
| 8,587,306 B2 * | 11/2013 | Takizawa ........... | G01R 33/4824 324/309 |
| 8,664,954 B2 * | 3/2014 | Hetzer .............. | G01R 33/4818 324/309 |
| 2003/0011369 A1 | 1/2003 | Brittain et al. | |
| 2003/0060698 A1 * | 3/2003 | Mistretta ................ | G01R 33/28 600/410 |
| 2008/0129289 A1 * | 6/2008 | Stemmer ............ | G01R 33/4824 324/309 |
| 2010/0117645 A1 * | 5/2010 | Eggers ............... | G01R 33/4824 324/309 |
| 2011/0025325 A1 * | 2/2011 | Li ...................... | G01R 33/4824 324/307 |

OTHER PUBLICATIONS

Japanese official action dated May 9, 2016 in corresponding Japanese Patent Application No. 2013-516280.
International Search Report in PCT/JP2012/061838, Jun. 2012.
M. Saranathan et al., "Azimuthal Sorting in Tandem with Elliptical Reordering (ASTER): a new k-space reordering scheme for reduced motion sensitivity", Proc. Intl. Soc. Mag. Reson. Med., Apr. 2009, 4605.
W. Lin et al., "High Temporal Resolution Radial Motion Correction with GROWL", Proc. Intl. Soc. Mag. Reson. Med., May 2010, 493.
M. Saranathan et al., "Non-contrast Outer Radial Inner Square k-space Scheme (NORISKS)—a breath-held balanced SSFP-Dixon technique for noncontrast enhanced renal MRA", Proc. Intl. Soc. Mag. Reson. Med., May 2011, 3347.
N. Takei et al., "Breathhold inhance inflow IR (BH-IFIR) with a novel 3D recessed fan beam View ordering", Proc. Intl. Soc. Mag. Reson. Med., May 2010, 1417.
M. S. Sussman et al., "SPRIAL-PR: A New Polar K-Space Trajectory for Flexible Variable-Density Sampling", Proc. Intl. Soc. Mag. Reson., 2005, 902.

* cited by examiner

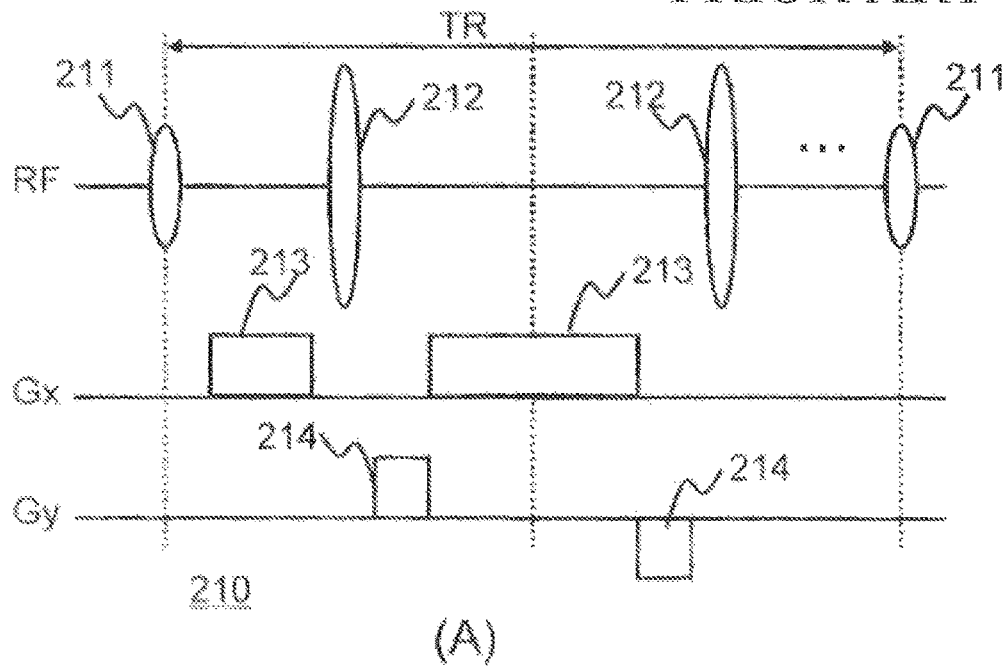
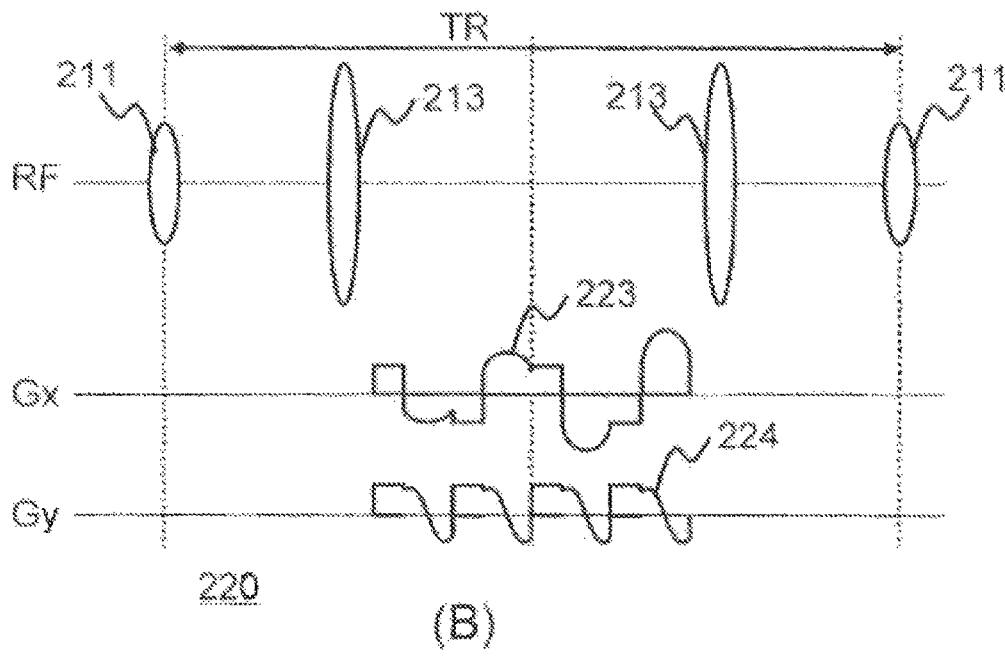
FIG. 4 PRIOR ART

FIG. 5
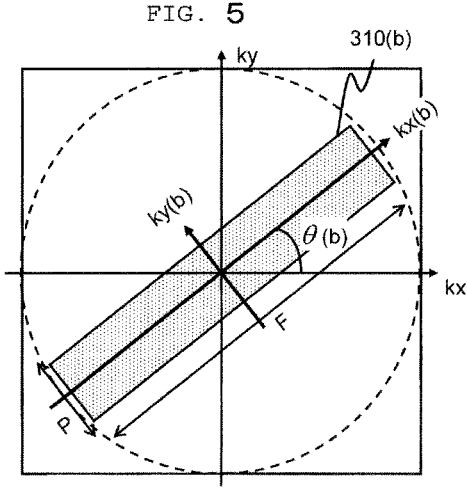
(A)
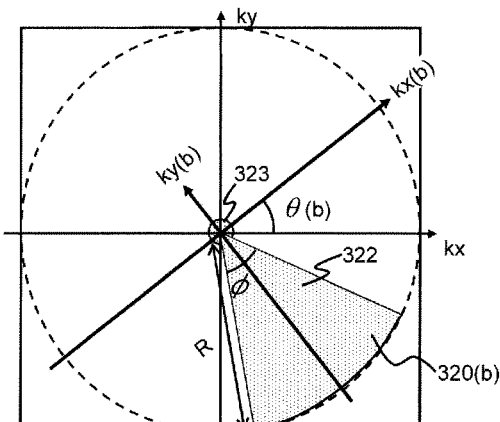
(B)

FIG.6
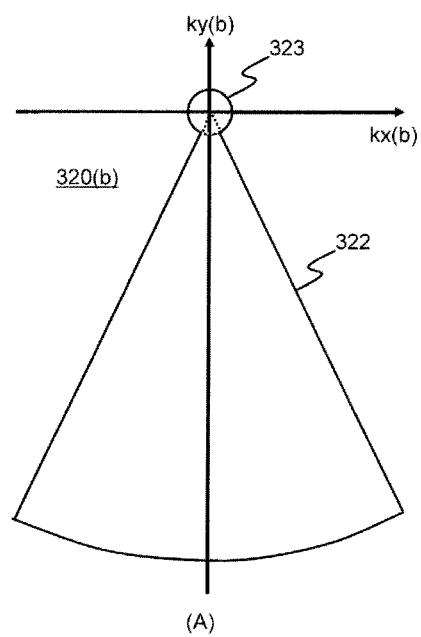
(A)
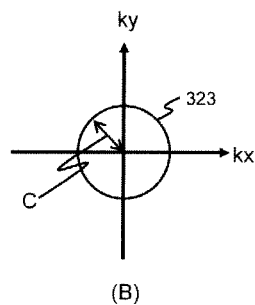
(B)

FIG.11
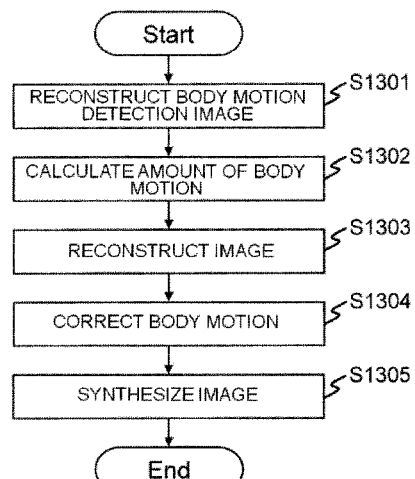
(A)
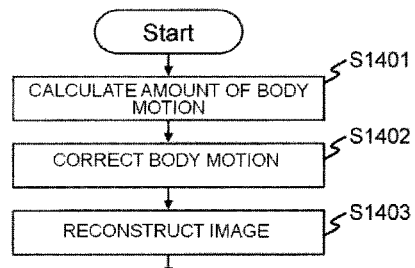
(B)

FIG.13
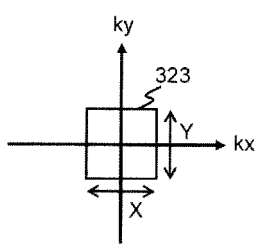
(A)
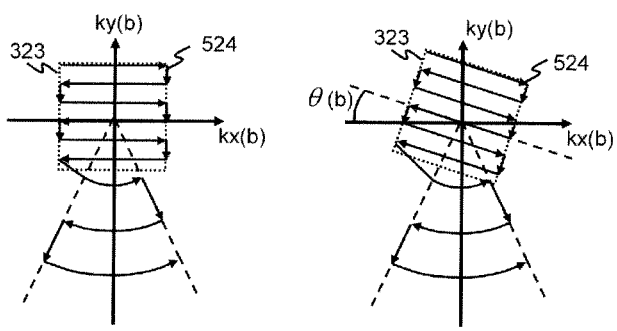
(B)          (C)

FIG.14
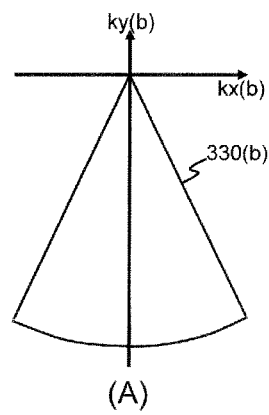
(A)
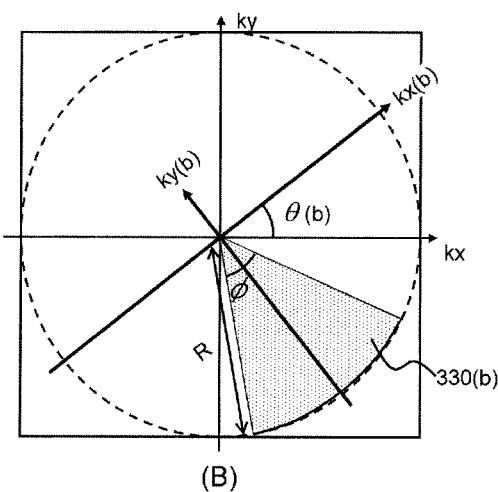
(B)

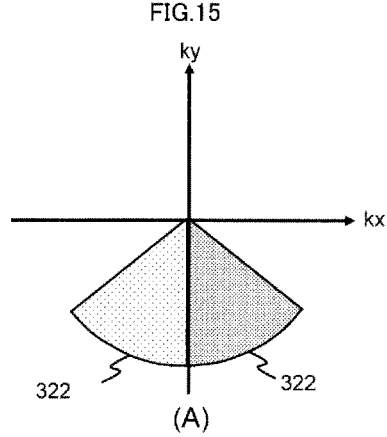
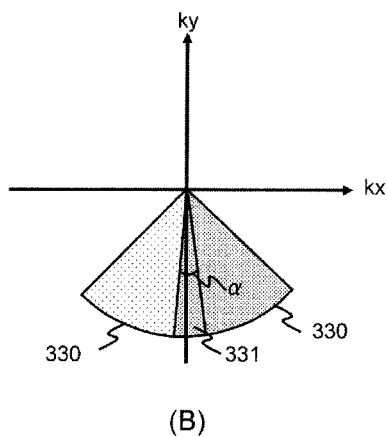
FIG.15

MAGNETIC RESONANCE IMAGING APPARATUS AND RECONSTRUCTED IMAGE ACQUISITION METHOD

TECHNICAL FIELD

The present invention relates to a nuclear magnetic resonance imaging (hereinafter, referred to as MRI) technology which measures a nuclear magnetic resonance (hereinafter, referred to as NMR) signal from hydrogen, phosphorus, or the like in an object and images a nuclear density distribution, a relaxation time distribution, or the like, and in particular, to a non-orthogonal system measurement technology.

BACKGROUND ART

An MRI apparatus for use in MRI is an apparatus which measures an NMR signal (echo signal) to be generated by nuclear spins constituting an object, in particular, a tissue of a human body, and images the form or function of the head, the abdomen, four limbs, or the like in a two-dimensional or three-dimensional manner. The echo signal is given different phase encode and frequency encode as positional information depending on a gradient magnetic field, and is arranged in a k space according to the positional information. The echo signal arranged in the k space is subjected to two-dimensional or three-dimensional Fourier transform, thereby reconstructing an image.

In MRI, the echo signal is measured so as to acquire data along a predetermined scan track of the k space. The scan track of the k space is classified roughly into a scan track by orthogonal system measurement which is determined by a gradient magnetic field pattern to be applied and acquires data on a k space of an orthogonal coordinate system, and a scan track by non-orthogonal system measurement which acquires data on a k space of a non-orthogonal coordinate system. The k space of the orthogonal coordinate system is a two-dimensional or three-dimensional data space which is defined by an orthogonal of two or three coordinate axes, and the k space of the non-orthogonal coordinate system is a two-dimensional or three-dimensional data space which is defined by size and declination. In the non-orthogonal system measurement, since the k space is scanned while changing the declination, near the center of the k space is repetitively scanned (for example, see NPL 1). Accordingly, this method is a robust measurement method in which the effect due to motion, such as breathing, is averaged, and no artifact is focused in a specific direction.

As an imaging method of MRI, an FSE method is known in which, after the application of a single excitation pulse, a plurality of reconvergence pulses are applied for TR until the application of the next excitation pulse to acquire a plurality of echo signals at high speed. In the FSE, the application of the single excitation pulse is referred to as a shot, and a plurality of echo signals obtained in one shot are referred to as an echo train. A method (hybrid radial method) which combines the non-orthogonal system measurement with the FSE method and obtains an image with few artifacts at high speed is known. In the hybrid radial method, each echo train is subjected to orthogonal system measurement inside the k space of the rectangular orthogonal coordinate system referred to as a single blade, and a blade is rotated inside the k space for each shot. In this case, the major axis direction of the blade corresponds to frequency encode, and the minor axis direction of the blade corresponds to phase encode.

As a measurement method which fills the k space at high speed, an EPI method is known in which measurement is made by combining a read gradient magnetic field in a frequency encode direction and a blip gradient magnetic field in a phase encode direction. The non-orthogonal system measurement may also be combined with the EPI method. In this case, the minor axis direction of the blade is referred to as frequency encode, and the major axis of the blade is referred to as phase encode (for example, see PTL 1). By the combination of both methods, it is possible to suppress artifacts, to reduce each application time of the frequency encode gradient magnetic field, and to reduce image strain.

CITATION LIST

Patent Literature

PTL 1: U.S. Pat. No. 7,535,222

Non Patent Literature

NPL 1: Magnetic Resonance in Medicine 42:963-969 (1999). Motion Correction With PROPELLER MRI: Application to Head Motion and Free-Breathing Cardiac Imaging. James G. Pipe.

SUMMARY OF INVENTION

Technical Problem

The contrast of a reconstructed image is determined by an echo signal arranged in the central region (low spatial frequency region) of the k space. Accordingly, when a measurement method which acquires a plurality of echo signals in one shot is used, control is performed such that an echo signal having desired contrast is arranged in a low spatial frequency region (lower range). The time from the application of the excitation pulse until an echo signal having desired contrast is obtained is referred to as effective TE.

On the other hand, in the non-orthogonal system measurement, since all echo signals are arranged near the lower range of the k space, an echo signal acquired for the time other than the effective TE is arranged in the lower range of the k space. For this reason, the resultant image decreases in contrast compared to the desired contrast.

If the k space is divided into a plurality of blades not overlapping each other to acquire data, when there is body motion between the blades, it is not possible to recognize the body motion, to perform appropriate correction, and to improve image quality.

The invention has been accomplished in consideration of the above-described situation, and an object of the invention is to improve contrast, to correct body motion, and to improve image quality in non-orthogonal measurement without sacrificing speed.

Solution to Problem

According to the invention, in imaging which combines a fast imaging sequence for acquiring a plurality of echo signals in one shot with non-orthogonal system measurement, the shape of a blade in which an echo train of each shot is arranged includes a fan-shaped region having the radius and the arc of a circle centered on the origin of the k space, and a region overlapping an adjacent blade. During measurement, control is performed such that an echo signal for desired TE of each blade is arranged in a low spatial frequency region of a k space, and during image reconstruction, body motion between the blades is corrected using data of the overlapping regions.

Advantageous Effects of Invention

According to the invention, it is possible to correct body motion at highspeed to improve contrast and image quality in non-orthogonal system measurement.

BRIEF DESCRIPTION OF DRAWINGS

FIG. 4(A) is an explanatory view illustrating an imaging sequence of the related art, and FIG. 4(B) is an explanatory view illustrating an imaging sequence of the first embodiment.

FIG. 5(A) is an explanatory view illustrating a rectangular blade of the related art, and FIG. 5(B) is an explanatory view illustrating a fan-shaped blade of the first embodiment.

FIG. 6(A) is an explanatory view illustrating the overall shape of the fan-shaped blade of the first embodiment, and FIG. 6(B) is an explanatory view illustrating a body motion detection region of the first embodiment.

FIG. 11(A) is a flowchart of an image reconstruction process of the first embodiment, and FIG. 11(B) is a flowchart of a modification of the image reconstruction process of the first embodiment.

FIG. 13(A) is an explanatory view illustrating a modification of a body motion detection region of the first embodiment, and FIGS. 13(B) and 13(C) are explanatory views illustrating a scan track of a modification.

FIGS. 14(A) and 14(B) are explanatory views illustrating a fan-shaped blade of a second embodiment.

FIG. 15(A) is an explanatory view illustrating the k space arrangement of the fan-shaped blade of the first embodiment, and FIG. 15(B) is an explanatory view illustrating the k space arrangement of the fan-shaped blade of the second embodiment.

DESCRIPTION OF EMBODIMENTS

First Embodiment

Figure 1:
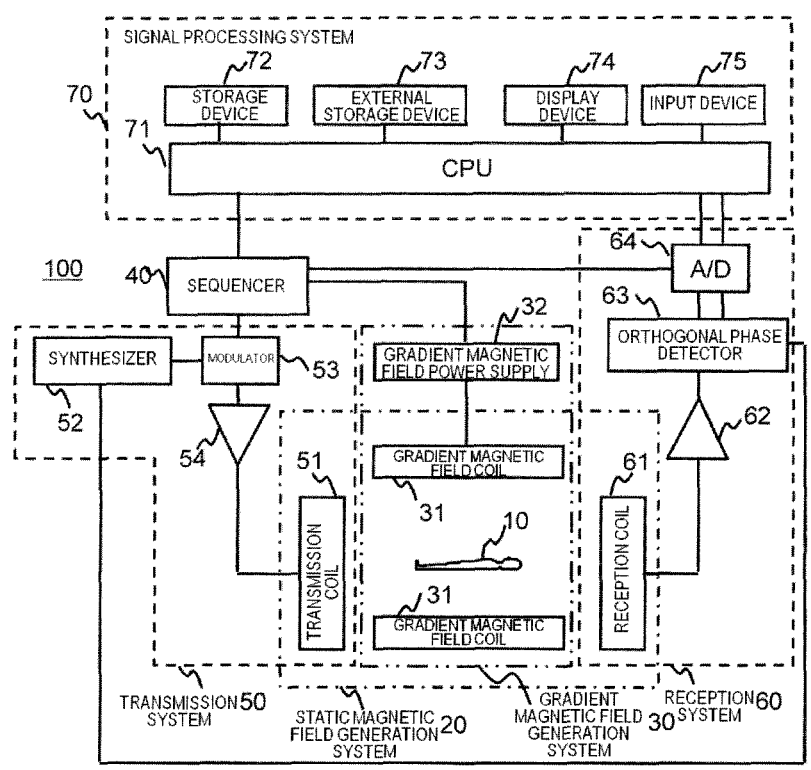
FIG. 1 is a block diagram showing the overall configuration of an MRI apparatus 100 of a first embodiment.

Hereinafter, a first embodiment to which the invention is applied will be described. Hereinafter, in all drawings for describing an embodiment of the invention, parts having the same functions are represented by the same reference numerals, and repetitive description will be omitted.

First, the outline of an MRI apparatus 100 of this embodiment will be described referring to FIG. 1. FIG. 1 is a block diagram showing the overall configuration of the MRI apparatus 100 of this embodiment. The MRI apparatus 100 of this embodiment obtains a tomographic image of an object using an NMR phenomenon, and includes a static magnetic field generation system 20, a gradient magnetic field generation system 30, a sequencer 40, a transmission system 50, a reception system 60, and a signal processing system 70.

The static magnetic field generation system 20 generates a uniform static magnetic field in a space around an object 10 in a direction perpendicular to the body axis in the case of a vertical magnetic field system and in a body axis direction in the case of a horizontal magnetic field system, and a permanent magnet-type, normal conducting, or superconducting static magnetic field generation source is arranged around the object 10.

The gradient magnetic field generation system 30 includes gradient magnetic field coils 31 which are wound in a triaxial direction of X, Y, and Z as a coordinate system (stationary coordinate system) of the MRI apparatus 100, and a gradient magnetic field power supply 32 which drives the respective gradient magnetic field coils 31. The gradient magnetic field generation system 30 drives the gradient magnetic field power supply 32 of the respective coils according to a command from a sequencer 40 described below to apply gradient magnetic fields Gx, Gy, and Gz in the triaxial direction of X, Y, and Z. During imaging, a gradient magnetic field pulse (Gs) in a slice direction is applied in a direction perpendicular to a slice surface (imaging section) to set a slice surface with respect to the object 10, and a gradient magnetic field pulse (Gp) in the phase encode direction and a gradient magnetic field pulse (Gf) in the frequency encode direction are applied in the remaining two orthogonal directions perpendicular to the slice surface to encode the positional information in the respective directions into the NMR signal (echo signal).

The sequencer 40 controls the gradient magnetic field generation system 30, the transmission system 50, and the reception system 60 so as to repetitively apply a high-frequency magnetic field pulse (hereinafter, referred to as "RF pulse") and a gradient magnetic field pulse according to a control signal from a CPU 71 provided in the signal processing system 70 described below.

The transmission system 50 irradiates the RF pulse onto the object 10 so as to excite nuclear magnetic resonance in the nuclear spins of an atom constituting a biological tissue of the object 10. The transmission system 50 includes a high-frequency oscillator (synthesizer) 52, a modulator 53, and a high-frequency amplifier 54, and a transmission-side high-frequency coil (transmission coil) 51. A high-frequency pulse output from the synthesizer 52 is amplitude-modulated by the modulator 53 at the timing according to an instruction from the sequencer 40, and the amplitude-modulated high-frequency pulse is amplified by the high-frequency amplifier 54 and supplied to the transmission coil 51 arranged near the object 10, whereby the RF pulse is irradiated onto the object 10.

The reception system 60 detects an echo signal (NMR signal) which is emitted by nuclear magnetic resonance of the nuclear spins constituting the biological tissue of the object 10. The reception system 60 includes a reception-side high-frequency coil (reception coil) 61, a signal amplifier 62, an orthogonal phase detector 63, and an A/D converter 64. An echo signal of a response of the object 10 induced by electromagnetic waves irradiated from the transmission coil 51 is detected by the reception coil 61 arranged near the object 10, then amplified by the signal amplifier 62, and divided into two systems of signals orthogonal to each other by the orthogonal phase detector 63 at the timing according to an instruction from the sequencer 40. Each of the two systems of signals is converted to a digital quantity by the A/D converter 64 and sent to the signal processing system 70.

The signal processing system 70 performs various data processes and the display, storage, and the like of the process results, and includes the CPU 71, a storage device 72, an external storage device 73, a display device 74, and an input device 75.

For example, the signal processing system 70 of this embodiment gives a control signal to the sequencer 40 according to an imaging sequence, and collects data for creating a tomographic image of the object 10 from the reception system 60. The motion of the object 10 being imaged is corrected using collected data (body motion correction) to reconstruct the tomographic image of the object 10. The imaging sequence is generated using an imaging parameter input from an operator through the input device 75 on the basis of a pulse sequence stored in advance in the storage device 72 or the like.

Figure 2:
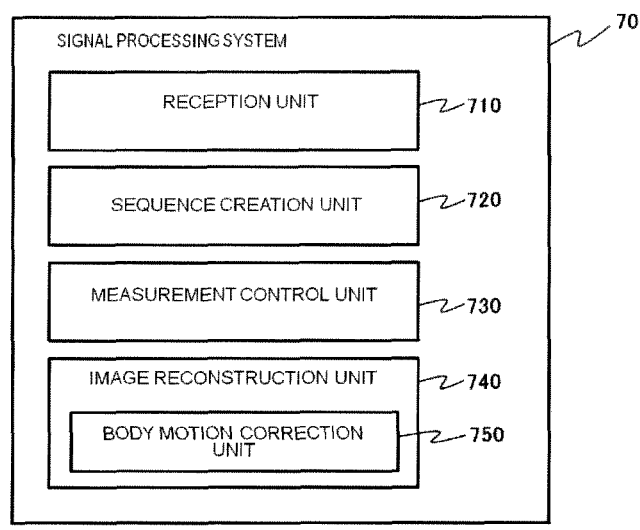
FIG. 2 is a functional block diagram of a signal processing system 70 of the first embodiment.

In order to implement this, as shown in FIG. 2, the signal processing system 70 of this embodiment includes a reception unit 710 which receives an imaging parameter from the operator, a sequence creation unit 720 which determines a gradient magnetic field shape of a pulse sequence stored in advance using the received imaging parameter to create an imaging sequence, a measurement control unit 730 which measures an echo signal according to the created imaging sequence and arranges the measured echo signal in the k space, and an image reconstruction unit 740 which reconstructs an image using the echo signal (data) arranged in the k space while performing body motion correction.

These functions are implemented when the CPU 71 loads and executes a program stored in advance in the storage device 72 or the like on a memory in the signal processing system 70.

The display device 74 displays the reconstructed tomographic image and constitutes an interface, which is used when the operator inputs various kinds of control information, along with the input device 75. The input device 75 is constituted by, for example, a trackball or a mouse, a keyboard, and the like. The storage device 72 and the external storage device 73 store information input from the operator, information generated in the middle of the process of the signal processing system 70 and through the process, and the like.

In FIG. 1, the transmission coil 51 and the gradient magnetic field coil 31 are arranged inside the static magnetic field space of the static magnetic field generation system 20, into which the object 10 is inserted, so as to face the object 10 in the case of the vertical magnetic field system and so as to surround the object 10 in the case of the horizontal magnetic field system. The reception coil 61 is arranged so as to face or surround the object 10.

At present, in regard to the type of nucleus to be imaged by the MRI apparatus, as one which is in widespread clinical use, there is a hydrogen nucleus (proton) which is a principal component of the object. Information regarding the spatial distribution of proton density or the spatial distribution of a relaxation time of an excitation state is imaged, thereby ing the form or function of the head, abdomen, four limbs, or the like of a human body in a two-dimensional or three-dimensional manner.

Figure 3:
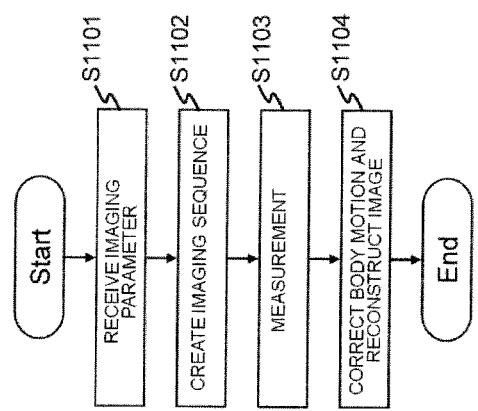
FIG. 3 is a flowchart of an imaging process of the first embodiment.

First, the flow of an imaging process during imaging by the MRI apparatus 100 of this embodiment using each function implemented by the signal processing system 70 will be described. FIG. 3 shows a process flow of the imaging process of this embodiment.

The reception unit 710 receives the imaging parameter input by the operator through the input device 75 (Step S1101). The input imaging parameter includes the number F of frequency encode steps (the number of samples in a frequency encode direction) and the number P of phase encode steps (the number of samples in a phase encode direction).

The sequence creation unit 720 determines the gradient magnetic field wave form using the imaging parameter and creates the imaging sequence from the pulse sequence stored in advance in the storage device 72 or the like (Step S1102). The measurement control unit 730 gives a command to the sequencer according to the imaging sequence, performs a measurement, and fills data in the k space (Step S1103). The image reconstruction unit 740 reconstructs an image while performing body motion correction (Step S1104).

In this embodiment, as a scan region during echo signal measurement, a fan-shaped blade which has a common region (overlapping region) in a low spatial frequency region of the k space is used, instead of a rectangular blade which is used in the hybrid radial method of the related art. The k space is scanned by a plurality of fan-shaped blades. A scan track inside each fan-shaped blade is determined such that an echo signal for desired TE is arranged in the low spatial frequency region of the k space, and the shape thereof is like a pendulum.

The sequence creation unit 720 determines a gradient magnetic field waveform for implementing the measurement and creates an imaging sequence. The measurement control unit 730 controls the respective units according to the created imaging sequence and executes the measurement. The image reconstruction unit 740 calculates the amount of body motion of the object 10 of each blade using data of the common region (overlapping region) of each of a plurality of fan-shaped blades and reconstructs an image while performing body motion correction.

Next, an imaging sequence creation process by the sequence creation unit 720 in Step S1102 mentioned above will be described.

First, an imaging sequence (referred to as a related art method), in which the hybrid radial method of non-orthogonal system measurement and the FSE method are combined, and a blade on the k space measured by the imaging sequence will be described. FIG. 4(A) is an imaging sequence 210 of the related art method. FIG. 5(A) shows a rectangular region (rectangular blade) 310 on the k space measured by the imaging sequence 210 shown in FIG. 4(A). Here, the respective axes of RF, Gx, and Gy represent the application timing of the RF pulse and the gradient magnetic field pulses in the biaxial direction.

In the FSE method, after the application of a single excitation RF pulse 211, a plurality of reconvergence RF pulses 212 are applied for the time TR until the next excitation RF pulse 211, and an echo signal is acquired each time each reconvergence RF pulse is applied. At this time, different phase encodes are given to the echo signals.

This is combined with the hybrid radial method, and for single TR (one shot), the rectangular region (rectangular blade) 310 including the origin of the k space shown in FIG.

5(A) is defined as a unit region, and a unit measurement for measuring the inside of the unit region is repeated while changing the angle (rotation angle θ) between the rectangular blade 310 and a kx axis of the k space in each shot, thereby measuring the entire k space. In the related art method, in order to implement this, the waveforms of gradient magnetic field pulses 213 and 211 are determined. As described above, the number B (where B is a natural number) of repetitions of measurement of one rectangular blade 310 (one shot) is set as an imaging parameter by the operator.

Here, a rectangular blade (b-th rectangular blade) which is measured by b-th (where b is a natural number which satisfies 1≤b≤B) repetition is represented by 310(b). The frequency encode direction of the rectangular blade 310(b) is referred to as a kx(b) axis and the phase encode direction of the rectangular blade 310(b) is referred to as a ky(b) axis. The angle between the x axis (kx axis) and the kx(b) axis of the k space is referred to as a rotation angle θ(b) of the rectangular blade 310(b). As described above, the number F of samples in the kx(b) axis direction and the number P of samples in the ky(b) axis direction of each rectangular blade 310(b) are respectively as imaging parameters (the number of frequency encodes and the number of phase encodes) by the operator.

In contrast, in this embodiment, for one shot of FSE, as a unit measurement, the inside of a fan-shaped blade (unit region) which has the same area (the same number of samples) as the rectangular blade 310(b) and has a common region in the low spatial frequency region of the k space is measured. Then, for each shot, the measurement is repeated while changing the angle (rotation angle θ) between the fan-shaped blade and the kx axis, thereby measuring the entire k space. At this time, the rotation angle θ is determined such that the fan-shaped blades do not overlap each other in a circumferential direction. An imaging sequence 220 of this embodiment for implementing this is shown in FIG. 4(B). The overall shape of a fan-shaped blade 320 of this embodiment is shown in FIG. 6(A), and the arrangement is shown in FIG. 5(B).

As shown in FIG. 6(A), the fan-shaped blade 320 of this embodiment includes a fan-shaped region 322 where data for reconstructing an image is collected, and a body motion detection region 323 where data for correcting body motion between the fan-shaped blades 320 is collected.

The fan-shaped region 322 is a region which is surrounded by two radii R and an arc between both radii R of a circle having a radius R centered on the origin of the k space, and partially overlaps the body motion detection region 323. As shown in FIG. 5(B), the central angle of the fan-shaped region 322 is referred to as φ [rad]. It is assumed that the ky(b) axis of a b-th fan-shaped blade 320(b) is on a line (central line) which bisects the central angle φ of the fan-shaped region 322(b) of the fan-shaped blade 320(b). It is assumed that the kx(b) axis is a direction perpendicular to the ky(b) axis. It is assumed that the rotation angle θ(b) of the fan-shaped blade 320(b) is the angle between the kx(b) axis and the kx axis.

As shown in FIG. 6(B), the body motion detection region 323 is an overlapping region which is common to all the fan-shaped blades 320 of each shot and is set in the low spatial frequency region determined in advance centered on the origin of the k space. In this embodiment, as an example, the body motion detection region 323 is defined as a circular region having a radius C.

As shown in FIG. 4(B), similarly to FSE of the related art, the imaging sequence 220 of this embodiment applies a plurality of reconvergence RF pulses 212 for the time TR until the application of the next excitation RF pulse 211 after the application of a single excitation RF pulse 211 and acquires an echo signal each time each reconvergence RF pulse is applied. At this time, as described above, for single TR, the inside of the fan-shaped blade 320 having the shape shown in FIG. 6 is measured, and the waveforms of gradient magnetic field pulses 223 and 224 in the Gx axis and Gy axis directions are determined such that a measurement is repeated while changing the rotation angle θ of the fan-shaped blade 320 for each TR to measure the entire k space. The waveforms of the gradient magnetic field pulses 223 and 224 in the Gx axis and Gy axis directions are determined such that, inside each fan-shaped blade 320, an echo signal having desired contrast is arranged in the low spatial frequency region of the k space.

Figure 7:
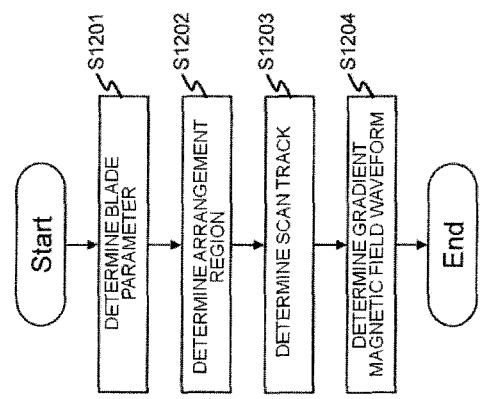
FIG. 7 is a flowchart of a sequence creation process of the first embodiment.

Hereinafter, the above-described gradient magnetic field shape by the sequence creation unit 720 of this embodiment is determined, and the flow of an imaging sequence creation process for creating an imaging sequence will be described referring to FIG. 7.

First, the sequence creation unit 720 calculates and determines the radius R of the fan-shaped region 322, the central angle φ, and the total number $B_{fan}$ of blades as blade parameters using the imaging parameters (blade parameter determination: Step S1201). The total number $B_{fan}$ of blades is the number of the fan-shaped blades 320 necessary for measuring the entire k space once.

First, the radius R is defined as F/2 (R=F/2) such that the final entire sampling area becomes equal to the entire sampling area by the rectangular blade 310.

Next, the central angle φ is determined as follows.

In this embodiment, for one shot, in order to measure the inside of the fan-shaped blade 320 instead of the rectangular blade 310 of the related art, similarly to the number of samples of the rectangular blade 310, the number of samples inside each fan-shaped blade 320 is determined by the number F of frequency encode steps and the number P of phase encode steps set as the imaging parameters by the operator, and is represented by FP.

First, it is considered that only the area S of the fan-shaped region 322 of the fan-shaped blade 320 is measured in one shot. As described above, the fan-shaped region is equal to the area FP of the rectangular blade 310.

Accordingly, the area S of the fan-shaped region 322 of the fan-shaped blade 320 is expressed by Expression (1) using the number F of samples and the number P of samples.

[Equation 1]

$$S = \pi \left(\frac{F}{2}\right)^2 \frac{\phi}{2\pi} = FP \tag{1}$$

If Expression (1) is solved in terms of φ, the central angle φ is expressed by Expression (2).

[Equation 2]

$$\phi = \frac{8P}{F} \tag{2}$$

In this embodiment, the fan-shaped region 322 of the fan-shaped blade 320 is determined so as to measure a region having the radius R of the k space without overlapping in the circumferential direction. Accordingly, as shown in Expression (3), the sampling area $N_{fan}$ inside the k space measured by the fan-shaped region 322 becomes equal to the area of a circle (radius R=F/2) which is inscribed in the k space.

[Equation 3]

$$N_{fan} = \pi R^2 = \frac{\pi}{4} F^2 \qquad (3)$$

Accordingly, the total number $B_{fan}$ of fan-shaped blades is expressed by Expression (4).

[Equation 4]

$$B_{fan} = \frac{N_{fan}}{S} = \frac{N_{fan}}{FP} = \frac{\pi R^2}{FP} = \frac{\pi}{4} \frac{F}{P} \qquad (4)$$

Accordingly, $1 \le b \le B_{fan}$. This is obtained by dividing $2\pi$ by the central angle $\phi$.

Since $0 \le \theta(b) < 2\pi$, the rotation angle $\theta(b)$ of the b-th fan-shaped blade 320(b) is expressed by Expression (5).

[Equation 5]

$$\theta(b) = (b-1) \times \frac{2\pi}{B_{fan}} + \Phi \qquad (5)$$

Here, $\Phi$ is a constant which defines a blade rotation angle of b=1.

Next, the sequence creation unit 720 divides the fan-shaped region 322 of the fan-shaped blade 320 in a radial direction according to the number of echo signals acquired in one shot and determines an arrangement region inside the fan-shaped blade 320 of each echo signal (Step S1202).

Figure 8:
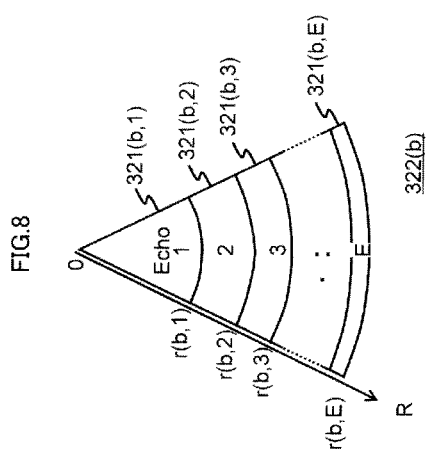
FIG. 8 is an explanatory view illustrating a divided region of the first embodiment.

Here, the number of echoes inside the fan-shaped blade 320 is referred to as E (where E is a natural number; E=P). As shown in FIG. 8, E echo signals are arranged in regions (divided regions) 321(n) (where n is a natural number which satisfies $1 \le n \le E$) having the same area which are obtained by dividing the fan-shaped region 322 of the fan-shaped blade 320 into E regions in the radial direction. Hereinafter, the divided regions of a fan-shaped region 322(b) of each b-th fan-shaped blade 320(b) are represented by 321(b,n).

In this embodiment, control is performed such that an echo signal having desired contrast is arranged in the low spatial frequency region of the k space, and other echo signals are arranged in a high spatial frequency region. Accordingly, control is performed such that an echo signal at desired timing (effective TE) is arranged in the low spatial frequency region of the divided region 321 near the origin of the k space.

The echo signal arrangement order of the divided region 321(b,n) inside the fan-shaped blade 320(b) changes depending on desired contrast. Here, for example, centric arrangement in which data is acquired in order from the central side of the k space will be described. That is, the divided region 321(b,1) where the first echo signal is arranged is defined as a radius r(b,1) of the fan-shaped region 322(b) of the fan-shaped blade 320(b), and the divided region 321(b,n) where the n-th echo signal is arranged is defined as a region between a radius r(b,n) and a radius r(b,n−1) of the fan-shaped blade 320(b). In the centric arrangement, r(b,E) is a radius R(b) of the fan-shaped region 322(b) of the fan-shaped blade 320(b).

Since the area of the divided region 321 (b,n) is the same, the radius r(b,n) is represented by Expression (6).

[Equation 6]

$$r(b, n) = R(b) \sqrt{\frac{n}{E}} \qquad (6)$$

Next, the sequence creation unit 720 determines a scan track inside each divided region 321(b,n) (Step S1203).

Figure 9:
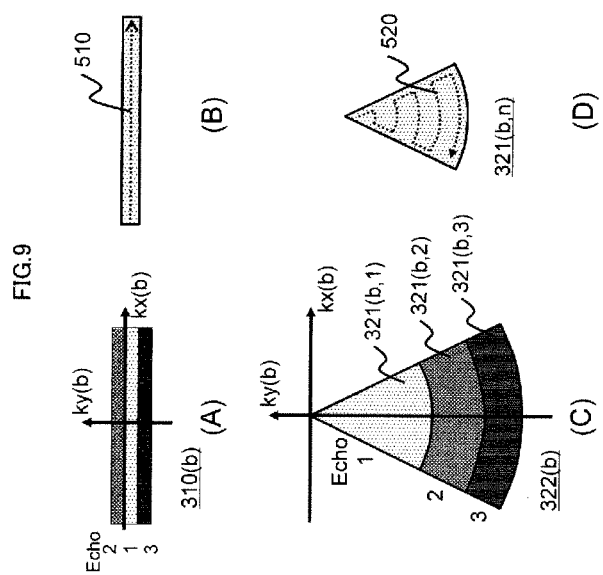
FIGS. 9(A) and 9(B) are explanatory views illustrating a scan track of an echo signal in the rectangular blade of the related art.
FIGS. 9(C) and 9(D) are explanatory views illustrating a scan track of an echo signal in the fan-shaped blade of the first embodiment.

In the rectangular blade 310(b) shown in FIG. 9(A), as shown in FIG. 9(B), one echo signal becomes a linear track (linear track 510). In this embodiment, as shown in FIG. 9(0), a scan track is set in each divided region 321 (b,n) inside the fan-shaped region 322(b) of the fan-shaped blade 320(b). As shown in FIG. 9(D), the scan track inside the divided region 321(b,n) is a series of tracks and defined as a pendulum-like track (pendulum-like track 520) which alternately has an arc-like portion of a concentric circle to the fan-shaped region 322(b) of the fan-shaped blade 320(b) and a linear portion, which is parallel to the radial direction and connects adjacent two arc-like portions.

The number of switching times in the frequency encode direction per echo signal in the divided region 321(b,n) of the fan-shaped region 322(b) of the fan-shaped blade 320(b) is defined as M(b,n).

Figure 10:
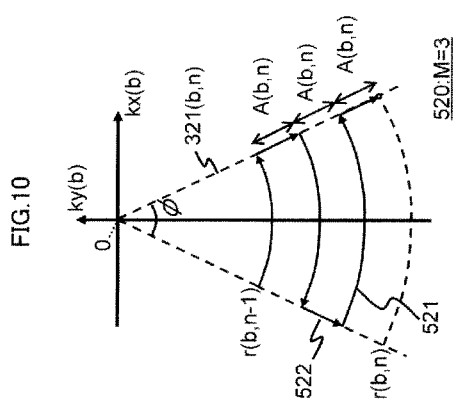
FIG. 10 is an explanatory view illustrating a pendulum-like track of the first embodiment.

An example of the pendulum-like track 520 set inside the divided region 321(b,n) when the number M(b,n) of switching times=3 is shown in FIG. 10. As shown in this drawing, the pendulum-like track 520 is constituted by an arc-like portion (arc-like track) 521 and a linear portion (linear track) 522 which are alternately repeated M times (in this case, three times).

An interval A(b,n) between the arc-like tracks 521 corresponding to the length of the linear track 522 is expressed by Expression (7) using the radius r(b,n) of the divided region 321(b,n) of the fan-shaped region 322(b) of the fan-shaped blade 320(b) and the number M(b,n) of switching times.

[Equation 7]

$$A(b, n) = \frac{r(b, n) - r(b, n-1)}{M(b, n)} \qquad (7)$$

A sampling length L(b,n) of the pendulum-like track 520 in each divided region 321(b,n) is the total of the arc-like tracks 521 and the linear tracks 522 of the number M(b,n) of switching times, and is thus expressed by Expression (8).

[Equation 8]

$$L(b, n) = \sum_{m=1}^{M(b,n)} (r(b, n-1) + (m-1)A(b, n))\phi(b) + \sum_{m=1}^{M(b,n)} A(b, n) \qquad (8)$$

Here, m is an integer which satisfies $1 \le m \le M$. Since the total sampling length of the pendulum-like tracks 520 inside the fan-shaped blade 320(b) is equal to the number F of samples (sampling length) in the frequency encode direction of the rectangular blade 310(*b*), the number M(b,n) of switching times of the divided region 321(*b,n*) of the fan-shaped region 322(*b*) of the fan-shaped blade 320(*b*) is expressed by Expression (9).

[Equation 9]

$$M(b, n) = \frac{(\phi - 2)(r(b, n) - r(b, n - 1)) + 2F}{\phi(r(b, n) + r(b, n - 1))} \quad (9)$$

From the above, the arc-like track 521 during m-th (a natural number which satisfies 1≤m≤M) switching in the divided region 321(*b,n*) of the fan-shaped region 322(*b*) of the fan-shaped blade 320(*b*) is expressed by Expression (10). However, −ϕ/2≤t≤ϕ/2.

[Equation 10]

$$\begin{cases} kx(b) = mA(b, n)\sin((-1)^m t) \\ ky(b) = mA(b, n)\cos((-1)^m t) \end{cases} \quad (10)$$

The linear track 522 during m-th switching in the divided region 321(*b,n*) of the fan-shaped region 322(*b*) of the fan-shaped blade 320(*b*) is expressed by Expression (11). However, (m−1)A(n)≤t≤mA(n).

[Equation 11]

$$\begin{cases} kx(b) = t\sin\left((-1)^m \frac{\phi(b)}{2}\right) \\ ky(b) = -t\cos\left((-1)^m \frac{\phi(b)}{2}\right) \end{cases} \quad (11)$$

In this embodiment, as described above, in order to correct the motion of the object 10 between the fan-shaped blades 320(*b*), data for body motion detection is acquired in the body motion detection region 323(*b*) of the central portion of the k space of each fan-shaped blade 320(*b*).

The body motion detection region 323 of this embodiment is a circle centered on the origin of the k space. If the radius is C, the body motion detection region 323 is expressed by Expression (12).

[Equation 12]

$$kx(b)^2 + ky(b)^2 \leq C^2 \quad (12)$$

The fan-shaped blade 320(*b*) of this embodiment includes a body motion detection region 323(*b*) in addition to the fan-shaped region 322(*b*). Accordingly, the radius of each divided region 321(*b*) changes like $r_{mc}$(b,n) shown in Expression (13) from r(b,n) shown in Expression (6) by adding the body motion detection region 323(*b*). r(b,n) in Expression (13) represents the radius of each divided region 321(*b,n*) defined by Expression (6).

[Equation 13]

$$r_{mc}(b, n) = \sqrt{r(b, n)^2 - \left(\frac{2\pi}{\phi} - 1\right)C^2} \quad (13)$$

The total sampling length L(b,1) of the first echo signal is the total of the track inside the circular body motion detection region 323(*b*) and the M(b,n)th arc-like track 521 and linear track 522, and is expressed by Expression (14). Here, ω represents an interval [pixel/sample] between sampling points inside the body motion detection region 323(*b*).

[Equation 14]

$$L(b, 1) = \omega T + \sum_{m=1}^{M}(m - 1)A(b, n)\phi + \sum_{m=1}^{M} A(b, n) \quad (14)$$

The total sampling length of the tracks in the divided region 321(*b*,1) including the body motion detection region 323(*b*) is equal to the sampling length F of the rectangular blade. Accordingly, M(b,1) is expressed by Expression (15).

[Equation 15]

$$M(b, 1) = \frac{(\phi - 2)r_{mc}(1) + 2(F - \omega T)}{\phi r_{mc}(1)} \quad (15)$$

If the arrangement region of each echo signal and the scan track are determined, the sequence creation unit 720 adds the rotation angle θ(b) of each fan-shaped blade 320(*b*) and determines the gradient magnetic field shape of each shot for the total number $B_{fan}$ of blades (Step S1204).

Here, the sequence creation unit 720 first creates a rotational matrix Rot(b) shown in Expression (16) using the rotation angle θ(b) of each fan-shaped blade 320(*b*).

[Equation 16]

$$Rot(b) = \begin{bmatrix} \cos\theta(b) & -\sin\theta(b) \\ \sin\theta(b) & \cos\theta(b) \end{bmatrix} \quad (16)$$

This is applied to the scan track of each echo signal, the scan track rotated in conformity with each fan-shaped blade 320(*b*) is calculated, and the waveforms of the gradient magnetic field pulses 223 and 224 in the biaxial (Gx, Gy) direction are determined.

The above-described pendulum-like track 520 is implemented by adding blip in the phase encode direction while switching the frequency encode direction during reading of one echo signal.

Through the above procedure, the sequence creation unit 720 of this embodiment determines a gradient magnetic field waveform to be measured using the imaging parameters set by the operator such that an echo signal having desired contrast is arranged in the low spatial frequency region of the k space inside each fan-shaped blade 320.

The measurement control unit 730 of this embodiment operates the respective units according to an instruction which is output from the signal processing system 70 according to the imaging sequence having the above-described gradient magnetic field waveform. That is, the rotation of each fan-shaped blade 320(*b*) from the kx axis by the rotation angle θ(b) and the measurement are repeated by the total number $B_{fan}$ of blades. At this time, control is performed such that an echo signal having desired contrast is arranged in the low spatial frequency region of the k space inside each fan-shaped blade 320(*b*).

Next, an image reconstruction process accompanied by body motion correction by the image reconstruction unit 740 of this embodiment in Step S1104 will be described. FIG. 11(A) shows a process flow of the image reconstruction process of this embodiment.

As shown in FIG. 2, the image reconstruction unit 740 of this embodiment includes a body motion correction unit 750 which performs body motion correction between blades using data (data for body motion detection) of the body motion detection region 323(b) of each fan-shaped blade 320(b). Body motion correction between blades is a process in which comparison is made among data for body motion detection of the respective fan-shaped blades 320(b), at least one of the amount of translation and the amount of rotation as the amount of body motion of the object 10 is detected, and blade data of each fan-shaped blade 320(b) is translated or rotated and corrected so as to cancel them.

In order to detect the amount of body motion of the object 10 in each fan-shaped blade 320(b), the image reconstruction unit 740 reconstructs an image using only k space data inside the body motion detection region 323 of each fan-shaped blade 320(b) (Step S1301). At this time, the image reconstruction unit 740 performs gridding on k space data filled in the body motion detection region 323 of each fan-shaped blade 320(b) on a lattice point of the orthogonal coordinate system of the k space and performs two-dimensional Fourier transform to reconstruct an image. Since it should suffice that the amount of body motion can be calculated, an image to be reconstructed may be an image having low spatial resolution. An image reconstructed from k space data of the body motion detection region 323(b) of each fan-shaped blade 320(b) is referred to as a body motion detection image (b).

Next, the image reconstruction unit 740 performs a body motion amount calculation process which causes the body motion correction unit 750 to calculate the amount of translation and the amount of rotation of each body motion detection image (b) as the amount of body motion for a reference image (Step S1302). For example, it is assumed that the reference image is a body motion detection image reconstructed from the body motion detection region 323(1) of the first fan-shaped blade 320(1). It is assumed that the amount of translation and the amount of rotation of each calculated body motion detection image (b) are the amount Δd(b) of translation and the amount Δq(b) of rotation of the fan-shaped blade 320 (b) in which the body motion detection image is obtained.

Next, the image reconstruction unit 740 reconstructs an image with desired resolution using k space data of the fan-shaped region 322(b) of each fan-shaped blade 320(b) (Step S1303). At this time, the image reconstruction unit 740 performs gridding on k space data filled in each fan-shaped blade 320(b) on the lattice point of the orthogonal coordinate system of the k space and performs two-dimensional Fourier transform to reconstruct an image. An image reconstructed from each fan-shaped blade 320(b) is referred to as an image (b).

Next, the image reconstruction unit 740 performs a body motion correction process in which each image (b) is translated and rotated by the amount Δd(b) of translation and the amount Δq(b) of rotation of each fan-shaped blade 320(b) (Step S1304).

The image reconstruction unit 740 synthesizes the images (b) after the correction to create a reconstructed image (Step S1305). In the process for synthesizing the images to create a reconstructed image, first, two-dimensional Fourier transform is performed on each image (b) after the correction to form blade k space data. This is repeated for each fan-shaped blade, and finally, gridding and two-dimensional Fourier transform are performed on all the fan-shaped blades to create a reconstructed image.

The image reconstruction unit 740 of this embodiment reconstructs an image while performing body motion correction through the above procedure.

As described above, according to this embodiment, since non-orthogonal system measurement is made, it is possible to reduce artifacts. Only a signal having desired contrast is arranged in the low spatial frequency region which determines contrast of the k space. Echo signals other than effective TE are arranged other than the low spatial frequency region. Accordingly, signals having different contrast are not mixed, and it is possible to obtain an image having desired contrast with high precision.

According to this embodiment, each fan-shaped blade has a common region in the low spatial frequency region of the k space. The amount of body motion of each fan-shaped blade with respect to a reference blade is calculated using data of the common region, and correction is performed so as to cancel the amount of body motion. Accordingly, according to this embodiment, correction of body motion between blades is also performed. Therefore, it is possible to reduce artifacts by body motion between blades.

Accordingly, according to this embodiment, it is possible to obtain a high-quality image having few artifacts and desired contrast at high speed.

The total number $B_{fan}$ of blades necessary for filling the perfect circular k space having the radius R (=F/2) of this embodiment is expressed by Expression (4). In the case of the rectangular blade 310 by the hybrid radial method of the related art, the total number $B_{rec}$ of blades necessary for filling the perfect circular k space having the radius R (=F/2) is obtained by Expression (17).

[Equation 17]

$$B_{rec} = \frac{\pi}{2} \frac{F}{P} \qquad (17)$$

Note that the sampling area $N_{rec}$ of the entire k space is expressed by Expression (18).

[Equation 18]

$$N_{rec} = FP \times B_{rec} = \frac{\pi}{2} F^2 \qquad (18)$$

In this way, when comparing Expression (4) and Expression (17), the number of blades necessary for scanning the area of the same k space (the perfect circular k space having the radius R) is ½ when the fan-shaped blade 320 is used compared to a case where the rectangular blade 310 is used, and the measurement time can be reduced. Accordingly, according to this embodiment, it is possible to improve filling efficiency of the k space and to reduce the measurement time.

In the case of measurement by a fan-shaped blade, an elliptical k space is filled, making it possible to perform rectangular perimetry which cannot be implemented in the rectangular blade. The sampling area $N_{fan}$ of this case is expressed by Expression (19).

[Equation 19]

$$N_{fan} = \pi RR' \le \frac{\pi}{4}F^2 \quad (19)$$

The total number $B_{fan}$ of fan-shaped blades 320(b) is expressed by Expression (20).

[Equation 20]

$$B_{fan} = \frac{N_{fan}}{S} = \frac{N_{fan}}{FP} = \frac{\pi RR'}{FP} \le \frac{\pi}{4}\frac{F}{P} \quad (20)$$

When comparing Expression (17) and Expression (19), in the measurement using the fan-shaped blade, even if rectangular perimetry is combined, it is possible to reduce the number of blades and to reduce the measurement time.

In this embodiment, for example, a case where a combination with the FSE sequence is made has been described.

However, in this embodiment, the scan region of the echo signal of each shot is defined as a fan-shaped blade, and the scan order and the scan track are determined as described above, thereby obtaining the above-described effects. Accordingly, it should suffice that the pulse sequence which is combined in this embodiment is a pulse sequence in which a plurality of echo signals are acquired for TR after the application of a single excitation pulse, and can be applied without depending on a sequence type or contrast.

In the foregoing embodiment, although the measurement control unit 730 measures the entire k space and then, the image reconstruction unit 740 reconstructs an image while performing body motion correction, the invention is not limited thereto. For example, if an image reconstructed from the body motion detection region 323(1) of the first fan-shaped blade 320(1) is defined as a reference image, in regard to the second or subsequent fan-shaped blade 320 (b) a configuration may be made such that an image is reconstructed while performing body motion correction each time each fan-shaped blade 320(b) is measured.

In the foregoing embodiment, although the image reconstruction unit 740 includes the body motion correction unit 750 and performs body motion correction using a reconstructed image during image reconstruction, body motion correction is not limited thereto. For example, a configuration may be made such that the amount of body motion is calculated using k space data of the body motion detection region 323 before image reconstruction, and k space data of the fan-shaped region 322 is subjected to body motion correction. The process flow of an image reconstruction accompanied by body motion correction in this case is shown in FIG. 11(B).

The body motion correction unit 750 uses k space data of the body motion detection region 323 (b) and calculates the amount of rotation and the amount of translation as the amount of body motion of k space data of the fan-shaped blade 320(b) (Step S1401). At this time, the amount of rotation is detected as the rotation angle from k space data of the body motion detection region 323(b) of the fan-shaped blade 320(b) as a reference. The amount of translation is detected as the phase difference from the k space data as a reference. The body motion correction unit 750 correct each piece of k space data so as to cancel the obtained amount of body motion (Step S1402).

The image reconstruction unit 740 uses k space data after the correction and performs a gridding process to reconstruct an image (Step S1403).

The radius C which defines the body motion detection region 323 may change according to the characteristic or the like of motion of a measured region. The radius C may change according to the amount of body motion calculated by the body motion correction unit 750. That is, when the amount of body motion is great, the body motion detection region 323 increases so as to increase precision, and when the amount of body motion is small, the body motion detection region 323 decreases. The amount of body motion as a reference for changing the radius C and the change amount of the radius C may be arbitrarily determined.

A configuration may be made such that the amount of body motion is calculated for each TR, that is, each time one fan-shaped blade 320(b) is calculated after the second fan-shaped blade, and the radius C is determined as described above.

Figure 12:
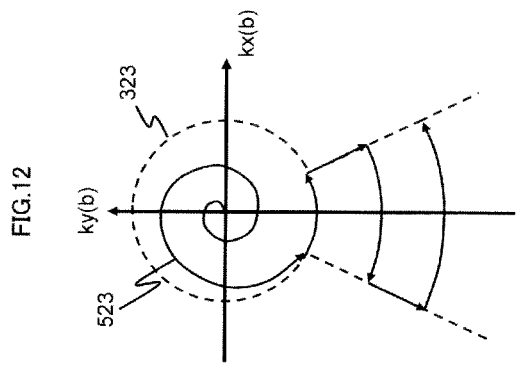
FIG. 12 is an explanatory view illustrating a modification of a scan track inside a body motion detection region of the first embodiment.

As shown in FIG. 12, the scan track inside the body motion detection region 323(b) in each fan-shaped blade 320(b) may be spiral (spiral scan). The scan track (spiral track 523) of the body motion detection region 323 in this case is expressed by Expression (21).

[Equation 21]

$$\begin{cases} kx(b) = R(t)\cos t \\ ky(b) = R(t)\sin t \end{cases} \quad (21)$$

Here, t is the number of samples (0≤t≤T), and R(t) is the distance from the origin of the k space (0≤R(t)≤C).

The shape of the body motion detection region 323 is not limited to a circular shape. For example, the shape of the body motion detection region 323 may be a rectangular shape having two sides parallel to the kx axis and two sides parallel to the ky axis. FIG. 13(A) shows the shape of the body motion detection region 323 when the body motion detection region 323 is rectangular. Here, it is assumed that the body motion detection region 323(b) is a rectangular shape in which one side has X pixels and the other side has Y pixels. FIGS. 13(B) and 13(C) show a scan track when the body motion detection region 323 is a rectangular shape. As shown in this drawing, when the shape of the body motion detection region 323 is rectangular, the scan track becomes a meandering track (meandering track 524).

The body motion detection region 323(b) in each fan-shaped blade 320(b) rotates according to the blade rotation angle θ(b) as shown in FIGS. 13(B) and 13(C).

As shown in FIG. 13(A), when the body motion detection region 323 is a rectangular shape, sampling on the same lattice point is performed in each fan-shaped blade 320(b) according to the meandering track 524.

Accordingly, comparison between the fan-shaped blades 320(b) during body motion detection is easily performed.

A configuration may be made such that, similarly to a case where the shape of the body motion detection region 323 is circular, the numbers X and Y of pixel of the respective sides when the body motion detection region 323 is a rectangular shape change according to the magnitude of motion of the measured region.

In the foregoing embodiment, for example, although the centric arrangement has been described as the echo signal arrangement order, the echo signal arrangement order is not limited thereto. An echo signal for desired TE (effective TE)

is determined so as to be arranged in the divided region 321(1) nearest the origin of the k space. With this configuration, it is possible to obtain an image having desired contrast.

For example, anti-centric data arrangement in which data is acquired in order from the outer circumference side may be made. Considering an acquisition order e ($1 \leq e \leq E$) of echo signals to be acquired for TR, while a divided region number n ($1 \leq n \leq N$) becomes n=e in the case of the centric arrangement, the divided region number n becomes n=E−e+1 in the case of the anti-centric arrangement.

Echo shift may be applied. In this case, the sequence creation unit 720 determines the divided region and the scan track by the same method as described above, and determines the gradient magnetic field shape when determining the gradient magnetic field shape of each shot in Step S1204 taking into consideration the echo arrangement order.

In this embodiment, multi-contrast measurement may be applied. The multi-contrast measurement is a measurement method in which two or more images having different contrast are acquired simultaneously by single measurement. For example, the multi-contrast measurement is implemented by acquiring two or more echo signals with a single pulse sequence and filling these echo signals in two or more k spaces.

The multi-contrast measurement is well used when TR is long, and a proton density weighted image (POW) and a T2 weighted image (T2W) are acquired simultaneously. Since the POW uses short effective TE, centric echo signal arrangement is used. Since the T2W uses comparatively lone TE, anti-centric or echo shift is used. When number of echo shifts when echo shift is used is automatically calculated according to effective TE of the T2W.

In this way, when this measurement is applied to the multi-contrast measurement, optimum echo signal arrangement according to TE of each image is used.

This embodiment may be combined with measurement which scans inside blades having different shapes.

For example, in the case of dynamic measurement in which improvement of resolution in the time direction is required, it is necessary to increase the data acquisition frequency of the lower range portion of the k space.

For this end, first, the fan-shaped blade 320 of this embodiment is used, base measurement as a reference is performed, and data of the entire internal region of the circle having the radius R of the k space is acquired. Thereafter, measurement by a concentric blade which is concentric region divided by a concentric circular circumference centered on the origin of the k space is repeated for every predetermined time. At this time, a plurality of concentric blades to be acquired once measure only the low spatial frequency region of the k space every time, and in the high spatial frequency region, a different region is measured every time. A region which is lacking every time uses data of the k space obtained by the base measurement.

With this configuration, k space data with only data of the lower range of the k space updated can be obtained for every predetermined time. Since a single measurement region is small compared to the entire region other than the first time, it is possible to reduce the measurement time. For this reason, it is possible to increase the number of repetitions within the same time and to improve resolution in the time direction of the dynamic measurement.

Second Embodiment

Next, a second embodiment to which the invention is applied will be described. In the first embodiment, the common body motion detection region is provided in the low spatial frequency region of the k space for all fan-shaped blades. In this embodiment, measurement is made while overlapping the fan-shaped blades in the circumferential direction, and the overlapping region is defined as body motion detection region.

An MRI apparatus of this embodiment is basically the same as in the first embodiment. Each functional configuration to be implemented by the signal processing system 70 is the same as in the first embodiment, and the imaging process by these functions is the same.

However, as described above, the shape of the blade to be measured for each TR is different. Accordingly, the blade parameter determination process for determining the shape of the blade by the sequence creation unit is different. Hereinafter, in this embodiment, description will be provided focusing on the blade parameter determination process by the sequence creation unit 720 different from the first embodiment.

First, the shape of a blade as a measurement region for single TR of this embodiment will be described.

In this embodiment, a fan-shaped blade 330 is measured for single TR.

As shown in FIG. 14(A), the fan-shaped blade 330 of this embodiment has the same shape as the fan-shaped region 322 of the fan-shaped blade 320 of the first embodiment.

As shown in FIG. 14(B), the fan-shaped blade 330 of this embodiment is a region which is surrounded by two radii R and an arc between both radii R of a circle having a radius R centered on the origin of the k space. The central angle of the fan-shaped blade 330 is referred to as φ [rad]. It is assumed that the ky(b) axis of a b-th fan-shaped blade 330(b) is on a line (central line) which bisects the central angle φ of the fan-shaped blade 330(b). It is assumed that the kx(b) axis is a direction perpendicular to the ky(b) axis. It is assumed that the rotation angle θ(b) of the fan-shaped blade 330(b) is the angle between the kx(b) axis and the kx axis.

In the first embodiment, as shown in FIG. 15(A), in the imaging sequence, the central angle φ [rad] and the rotation angle θ(b) of the fan-shaped blade 320(b) are determined such that the entire region having the radius R of the k space is measured without causing the fan-shaped region 322 of each fan-shaped blade 320 to overlap the fan-shaped region 322 of the adjacent fan-shaped blade 320.

Meanwhile, in this embodiment, as shown in FIG. 15(B), each fan-shaped blade 330(b) has a region (overlapping region 331) which overlaps the adjacent fan-shaped blade 330 in the circumferential direction, and the central angle φ [rad] and the rotation angle θ(b) are determined such that the entire region having the radius R of the k space is measured.

The central angle α of the overlapping region 331 is defined by the ratio with respect to the blade central angle φ.

The ratio is set in advance to, for example, 10% or the like.

Figure 16:
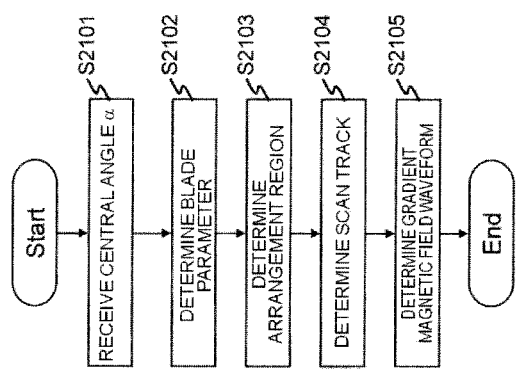
FIG. 16 is a flowchart of a sequence creation process of the second embodiment.

The flow of the blade parameter determination process by the sequence creation unit 720 of this embodiment is shown in FIG. 16.

The sequence creation unit 720 of this embodiment receives the setting of the central angle α of the overlapping region 331 prior to determining the blade parameters (Step S2101).

The sequence creation unit 720 uses the imaging parameters such that the overlapping region 331 having the set central angle α is implemented, and calculates and determines the radius R of the fan-shaped region 322, the central angle φ, and the total number $B_{fan}$ of blades as the blade parameters (blade parameter determination: Step S2102).

As in the first embodiment, the radius R of the fan-shaped blade 330 is F/2. F is the number of samples in the frequency encode direction of the rectangular blade 310.

First, the central angle φ and the total number $B_{fan}$ of blades of the fan-shaped blade 330 when there is no overlapping region are determined. These are calculated by Expression (4) and Expression (2) similarly to the calculation method of the total number $B_{fan}$ of blades and the central angle φ of the fan-shaped region 332 in the first embodiment.

The overlapping region 331 of the central angle α is implemented by increasing either the total number $B_{fan}$ of blades or the blade central angle φ when the fan-shaped blade 330 is arranged with no overlapping region.

When increasing the total number $B_{fan}$ of blades, a total number $B_{fan}'$ of blades after the increase is obtained by Expression (22) using the central angle φ obtained by Expression (2) and the central angle α of the overlapping region 331.

[Equation 22]

$$B'_{fan} = \frac{2\pi}{\phi - \alpha} \quad (22)$$

At this time, the rotation angle θ(b) of each fan-shaped blade 330(b) is obtained by Expression (23).

[Equation 23]

$$\theta(b) = (\phi - \alpha)(b-1) \quad (23)$$

When increasing the blade central angle φ, a blade central angle φ' after the increase is expressed by Expression (24).

[Equation 24]

$$\phi' = \phi + \alpha \quad (24)$$

At this time, the rotation angle θ(b) of each fan-shaped blade 330(b) is obtained by Expression (25).

[Equation 25]

$$\theta(b) = \phi'(b-1) \quad (25)$$

The sequence creation unit 720 of this embodiment determines the total number of blades, the central angle, the rotation angle (($B_{fan}'$, φ, θ(b)) or ($B_{fan}$, φ', θ(b))) in the above-described manner.

Similarly to the fan-shaped region 322 of the first embodiment, the sequence creation unit 720 divides the fan-shaped blade 330 of this embodiment in the radial direction and determines the arrangement region inside the fan-shaped blade 330 of each echo signal (Step S2103). The determination method is the same as in the first embodiment.

The sequence creation unit 720 determines the scan track inside each divided region 321 (Step S2104). In this embodiment, since the body motion detection region 323 is not provided, the scan track of this embodiment is the same as the pendulum-like track 520 inside the fan-shaped region 322 before taking into consideration the body motion detection region 323 of the first embodiment.

If the arrangement region of each echo signal and the scan track are determined, the sequence creation unit 720 adds the rotation angle θ(b) of each fan-shaped blade 330(b) and determines the gradient magnetic field shape of each shot for $B_{fan}$ or $B_{fan}'$ times by the same method as in the first embodiment (Step S2105).

Next, an image reconstruction process accompanied by body motion correction by the image reconstruction unit 740 of this embodiment will be described. The image reconstruction process of this embodiment is basically the same as the image reconstruction process of the first embodiment.

That is, in this embodiment, in order to detect the amount of body motion of the object in each fan-shaped blade 330(b), the image reconstruction unit 740 uses only k space data inside each overlapping region 331 to reconstruct an image. At this time, the image reconstruction unit 740 performs gridding on k space data filled in each overlapping region 331 on a lattice point of the orthogonal coordinate system of the k space and performs two-dimensional Fourier transform to reconstruct an image. Since it should suffice that the amount of body motion can be calculated, an image to be reconstructed may be an image of low spatial resolution. An image reconstructed from k space data of the overlapping region 331 of each fan-shaped blade 330(b) is referred to as a body motion detection image b.

Next, the image reconstruction unit 740 performs a body motion amount calculation process which causes the body motion correction unit 750 to calculate the amount of translation and the amount of rotation of each body motion detection image (b) as the amount of body motion with respect to a reference image. It is assumed that the reference image is, for example, a body motion detection image (1) reconstructed from the overlapping region 331 of the first fan-shaped blade 330(1) and an adjacent fan-shaped blade 330(b).

In this embodiment, since the overlapping region 331 is a common region only between adjacent fan-shaped blades 330, the amount of body motion with respect to an adjacent fan-shaped blade is calculated in order from the fan-shaped blade 330 adjacent to the fan-shaped blade 330 in which the reference image is obtained, and added to the amount of body motion with respect to the reference image of the adjacent fan-shaped blade, thereby obtaining the amount of body motion with respect to the reference image.

That is, if the amount of body motion between the b-th fan-shaped blade 330(b) and the (b−1)th fan-shaped blade 330(b−1) is referred to as ΔDb (ΔDb=(Δx,Δy,Δz,Δα,Δβ,Δγ); x, y, and z are the amount of translation, and α, β, and γ are the amount of rotation), an apparent amount $\Delta D_{b+1}$ of body motion in the (b+1)th fan-shaped blade 330(b+1) is expressed by $D_{b+1} = D_b + \Delta D_b$. Accordingly, the apparent amount of body motion of each of the fan-shaped blades 330 is obtained from the amount of body motion of the fan-shaped blade 330 measured previously from Expression (26).

[Equation 26]

$$\begin{aligned} D_{b+1} &= D_b + \Delta D_b \\ &= (D_{b-1} + \Delta D_{b-1}) + \Delta D_b \\ &\vdots \\ &= \sum_{m=1}^{b} \Delta D_m \end{aligned} \quad (26)$$

Here, $D_1 = 0$

Subsequent body motion correction using the amount of body motion of each fan-shaped blade 330(b) by the image reconstruction unit 740 is the same as in the first embodiment. That is, an image is reconstructed using k space data of each fan-shaped blade 330(b), and body motion correction is performed using the amount of body motion of each fan-shaped blade, thereby obtaining a reconstructed image. Alternatively, body motion correction is performed on k space data of each fan-shaped blade 330(b), thereby obtaining a reconstructed image.

As described above, according to this embodiment, as in the first embodiment, a high-quality image having few artifacts and desired contrast can be obtained at high speed.

In this embodiment, as in the first embodiment, a configuration may be made such that image reconstruction accompanied by body motion correction is performed for each measurement of each fan-shaped blade 330.

In this embodiment, as in the first embodiment, the body motion correction unit 750 may be configured to calculate the amount of body motion using k space data of the overlapping region 331 and to perform body motion correction. In this case, as in the first embodiment, the image reconstruction unit 740 reconstructs an image from k space data after body motion correction.

In this embodiment, similarly to the body motion detection region 323 of the first embodiment, the central angle α of the overlapping region 331 may be adjusted according to the magnitude of the calculated amount of body motion. That is, when the amount of body motion is great, the central angle α changes such that the overlapping region 331 increases so as to increase precision. When the amount of body motion is small, the central angle α changes to decrease. A reference value for discriminating the magnitude of the amount of body motion and the change amount of the central angle α are determined in advance.

A configuration may be made such that the amount of body motion is calculated for each TR, and the central angle α of the overlapping region 331 for next TR changes according to the calculation result.

The fan-shaped blade 330 of this embodiment may further include the body motion detection region 323 of first embodiment.

In this case, the body motion correction unit 750 of the image reconstruction unit 740 uses data of both the body motion detection region 323 and the overlapping region 331, and detects the amount of body motion.

In the foregoing embodiments, although the signal processing system 70 of the MRI apparatus 100 may be configured so as to calculate the gradient magnetic field waveform implementing k space scan with the fan-shaped blades from the imaging conditions, the invention is not limited thereto. A configuration may be made such that a gradient magnetic field waveform is calculated on an information processing apparatus which can perform data transmission and reception with the MRI apparatus 100 and is separated from MRI apparatus.

In the foregoing embodiments, although the sequence creation unit 720 calculates the parameters of the fan-shaped blades each time the imaging parameter is set during imaging and calculates the gradient magnetic field waveform, the invention is not limited thereto. For example, a configuration may be made such that the gradient magnetic field shape may be calculated for each imaging parameter which is likely to be used and stored as a database in the storage device 72 or the like in association with the imaging parameter. In this case, if the imaging parameter is received during imaging, in Step S1102, the sequence creation unit 720 extracts the gradient magnetic field shape stored in association with the received imaging parameter with reference to the database and creates an imaging sequence.

In the foregoing embodiments, although a region where data for reconstructing an image is obtained is a fan-shaped region which is surrounded by two radii R and an arc between both radii R of the circle having the radius R centered on the origin of the k space, the invention is not limited thereto. It should suffice that a region is surrounded by two line segments with the origin of the k space as a starting point and a line connecting the other end points of the two line segments.

REFERENCE SIGNS LIST

10: object, 20: static magnetic field generation system, 30: gradient magnetic field generation system, 31: gradient magnetic field coil, 32: gradient magnetic field power supply, 40: sequencer, 50: transmission system, 51: transmission coil, 52: synthesizer, 53: modulator, 54: high-frequency amplifier, 60: reception system, 61: reception coil, 62: signal amplifier, 63: orthogonal phase detector, 64: A/D converter, 70: signal processing system, 71: CPU, 72: storage device, 73: external storage device, 74: display device, 75: input device, 100: MRI apparatus, 210: imaging sequence, 211: excitation RF pulse, 212: reconvergence RF pulse, 213: gradient magnetic field pulse, 220: imaging sequence, 223: gradient magnetic field pulse, 310: rectangular blade, 320: fan-shaped blade, 321: divided region, 322: fan-shaped region, 323: body motion detection region, 330: fan-shaped blade, 331: overlapping region, 332: fan-shaped region, 510: linear track, 520: pendulum-like track, 521: arc-like track, 522: linear track, 523: spiral track, 529: meandering track, 710: reception unit, 720: sequence creation unit, 730: measurement control unit, 790: image reconstruction unit, 750: body motion correction unit

The invention claimed is:

1. A magnetic resonance imaging apparatus comprising:
   a static magnetic field generation unit which generates a static magnetic field;
   a magnetic field application unit which applies a gradient magnetic field and a high-frequency magnetic field to a desired imaging region of an object arranged in the static magnetic field;
   a detection unit which detects an echo signal from the desired imaging region;
   a measurement control unit which controls the magnetic field application unit and the detection unit and measures the echo signal so as to acquire data of a predetermined region inside a k space; and
   an image reconstruction unit which reconstructs an image of the imaging region using data of the k space,
   wherein the measurement control unit performs control such that a unit measurement to measure a plurality of pieces of data of a unit region within 1 TR is repeated while rotating the unit region by a rotation angle determined in advance centered on the origin of the k space for each unit measurement,
   in the unit measurement, an echo signal having desired contrast is arranged in a low spatial frequency region of the k space,
   the unit region includes a first region surrounded by two line segments with the origin of the k space as a starting point and a line connecting the other end points of the two line segments, and a region overlapping an adjacent unit region, and
   the image reconstruction unit includes a body motion correction unit which performs body motion correction when reconstructing the image using data of the overlapping region.

2. The magnetic resonance imaging apparatus according to claim 1, wherein the two line segments are the radius of a circle centered on the k space, and the line connecting the end points is an arc of the circle.

3. The magnetic resonance imaging apparatus according to claim 2, wherein the overlapping region is a region which is set in the low spatial frequency region of the k space and has the same shape with respect to the entire unit region.

4. The magnetic resonance imaging apparatus according to claim 3, wherein the rotation angle of each unit region is determined such that the first region is arranged in a circumferential direction of the circle centered on the origin of the k space without overlapping.

5. The magnetic resonance imaging apparatus according to claim 1, wherein the rotation angle of each unit region is determined such that the first region is arranged so as to have an overlapping region at a central angle determined in advance in a circumferential direction of the circle centered on the origin of the k space.

6. The magnetic resonance imaging apparatus according to claim 2, further comprising:

an imaging condition reception unit which receives an imaging condition from an operator; and an imaging sequence generation unit which generates an imaging sequence from the received imaging condition, wherein the measurement control unit performs the control according to the imaging sequence, and the imaging sequence generation unit includes a parameter determination unit which determines the radius of the circle centered on the origin of the k space, a central angle as the angle between the two line segments, and the total number of unit regions which is the number of unit regions having different rotation angles, a region determination unit which determines an arrangement region of each echo signal for each unit measurement, a scan track determination unit which determines a scan track inside each determined arrangement region, and a waveform determination unit which determines the scan track of each unit measurement according to a rotation angle as the angle between each unit region and a coordinate axis determined in advance of the k space and determines the gradient magnetic field waveform of the imaging sequence.

7. The magnetic resonance imaging apparatus according to claim 6, wherein the radius of the circle centered on the origin of the k space is determined by the number of frequency encodes, the central angle is determined by the diameter of the circle and the total number of pieces of data inside the unit region, and the total number of unit regions is equal to or greater than a value which is obtained by dividing $2\pi$ by the central angle.

8. The magnetic resonance imaging apparatus according to claim 6, wherein the scan track inside each arrangement region is like a pendulum.

9. The magnetic resonance imaging apparatus according to claim 1, wherein the body motion correction unit calculates the amount of body motion of an image of each unit region on the image obtained by reconstructing data of the overlapping region, and corrects a reconstructed image from data of each unit region so as to cancel the calculated amount of body motion.

10. The magnetic resonance imaging apparatus according to claim 1, wherein the body motion correction unit calculates the amount of body motion of each unit region on the k space using data of the overlapping region, and corrects data of each unit region so as to cancel the calculated amount of body motion, and the image reconstruction unit reconstructs an image from data after the correction.

11. The magnetic resonance imaging apparatus according to claim 1, wherein the overlapping region is determined according to the amount of body motion calculated by the body motion correction unit.

12. The magnetic resonance imaging apparatus according to claim 3, wherein the overlapping region is a region inside the circle centered on the origin of the k space.

13. The magnetic resonance imaging apparatus according to claim 3, wherein the overlapping region is a rectangular region which is centered on the origin of the k space and each side of which is parallel to either of a kx axis and a ky axis.

14. A reconstructed image acquisition method in a magnetic resonance imaging apparatus, the reconstructed image acquisition method comprising:

unit measurement which acquires data of a unit region;

repetitive measurement which reconstructs the unit measurement while rotating the unit region at a rotation angle determined in advance centered on the origin of a k-space; and image reconstruction which reconstructs an image from data obtained in the repetitive measurement, wherein the unit region includes a first region surrounded by two line segments with the origin of the k space as a starting point and a line connecting the other end points of the two line segments, and a region overlapping an adjacent unit region, and image reconstruction includes body motion amount calculation which calculates the amount of body motion of each unit region on an image reconstructed from data of the overlapping region of each unit region, body motion correction which corrects an image reconstructed from data of the first region of each unit region using the amount of body motion of the unit region, and image synthesis which synthesizes an image after correction of each unit region.

15. A reconstructed image acquisition method in a magnetic resonance imaging apparatus, the reconstructed image acquisition method comprising:

unit measurement which acquires data of a unit region;

repetitive measurement which repeats the unit measurement while rotating the unit region at a rotation angle determined in advance centered on the origin of a k-space; and image reconstruction which reconstructs an image from data obtained in the repetitive measurement, wherein the unit region includes a first region surrounded by two line segments with the origin of the k space as a starting point and a line connecting the other end points of the two line segments, and a region overlapping an adjacent unit region, and the image reconstruction includes body motion amount calculation which calculates the amount of body motion of each unit region on data of the overlapping region of each unit region, body motion correction which corrects data of the first region of each unit region using the amount of body motion of the unit region, and image reconstruction which reconstructs an image from data after the correction of each unit region.

* * * * *

UNITED STATES PATENT AND TRADEMARK OFFICE
CERTIFICATE OF CORRECTION

| | | |
|---|---|---|
| PATENT NO. | : 9,513,356 B2 | Page 1 of 1 |
| APPLICATION NO. | : 14/113259 | |
| DATED | : December 6, 2016 | |
| INVENTOR(S) | : Yasuhiro Kamada et al. | |

It is certified that error appears in the above-identified patent and that said Letters Patent is hereby corrected as shown below:

On the Title Page

Add the following:
-- (30) Foreign Application Priority Data
May 20, 2011   [JP] ..................... 2011-113891. --

Signed and Sealed this
Twenty-fifth Day of April, 2017

Michelle K. Lee
*Director of the United States Patent and Trademark Office*